(12) United States Patent
Johnson

(10) Patent No.: US 6,171,285 B1
(45) Date of Patent: Jan. 9, 2001

(54) RETRACTABLE SYRINGE

(76) Inventor: R. Steven Johnson, P.O. Box 1875, Jena, LA (US) 71342

( * ) Notice: Under 35 U.S.C. 154(b), the term of this patent shall be extended for 0 days.

(21) Appl. No.: 09/414,296

(22) Filed: Oct. 6, 1999

(51) Int. Cl.[7] .................................................... A61M 5/00

(52) U.S. Cl. ........................... 604/195; 604/110; 604/241

(58) Field of Search ................................... 604/195, 192, 604/218, 187, 110, 220, 240, 241

(56) References Cited

U.S. PATENT DOCUMENTS

| | | | |
|---|---|---|---|
| 4,026,287 | 5/1977 | Haller | 128/215 |
| 4,995,874 | 2/1991 | Strickland | 604/195 |
| 5,141,495 | 8/1992 | Clovson | 604/110 |
| 5,417,661 | 5/1995 | Stringer | 604/110 |
| 5,533,970 | 7/1996 | Berger | 604/110 |
| 5,593,391 | 1/1997 | Stanners | 604/232 |

*Primary Examiner*—John D. Yasko
(74) *Attorney, Agent, or Firm*—John M. Harrison

(57) ABSTRACT

A retractable syringe characterized by a syringe needle which can be retracted into the barrel of the syringe and locked therein after use, to prevent accidental needle sticks or re-use of the syringe. In a preferred embodiment the syringe barrel is terminated by a tapered barrel neck which communicates with the syringe barrel interior and threadibly receives the needle hub of a cannulated syringe needle. A syringe plunger, slidably disposed in the syringe barrel, is terminated by a plunger nipple for threadibly engaging the interior of the needle hub. After the syringe plunger is operated to expel the liquid contents of the syringe barrel through the syringe needle, the plunger is rotated in the barrel to threadibly seat the plunger nipple in the needle hub. Continued rotation of the plunger in the barrel threads the attached needle hub and needle into the syringe barrel. In a preferred embodiment a pair of flexible plunger lock tabs is fitted on the plunger. A pair of plunger lock pins is inserted between the plunger lock tabs to extend the plunger lock tabs outwardly from the plunger and cause the plunger lock tabs to engage a locking ridge shaped circumferentially inside the barrel, and thus hinder removal of the retracted plunger and attached contaminated syringe needle from the barrel. In another embodiment a pair of lock plates is provided on the plunger for engaging the locking ridge and hindering removal of the plunger and needle.

20 Claims, 2 Drawing Sheets

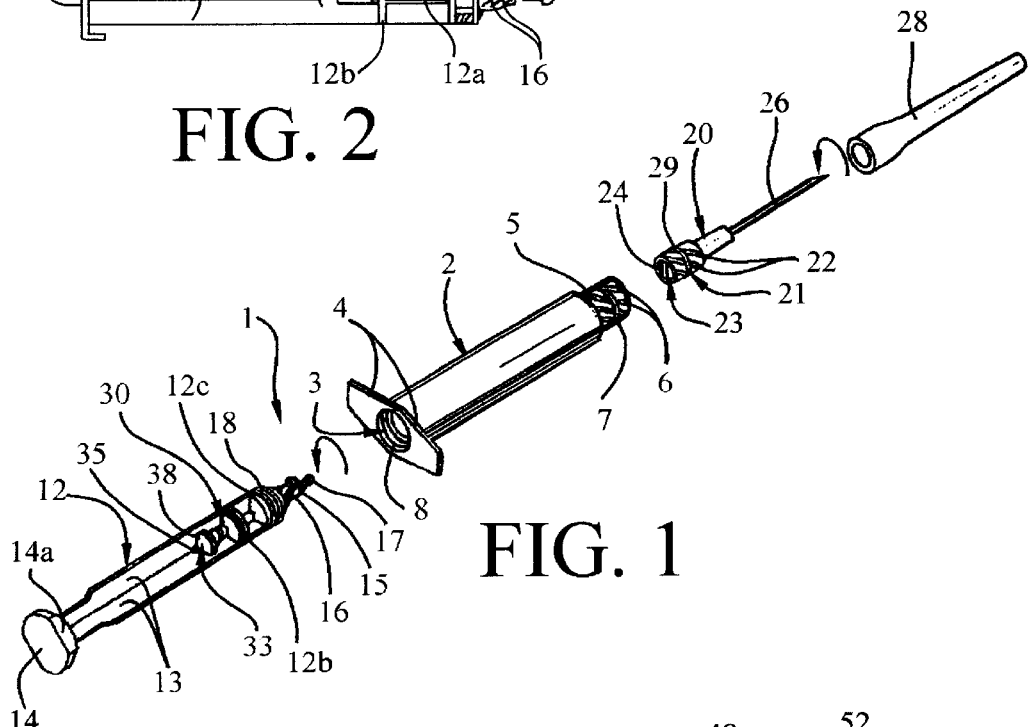
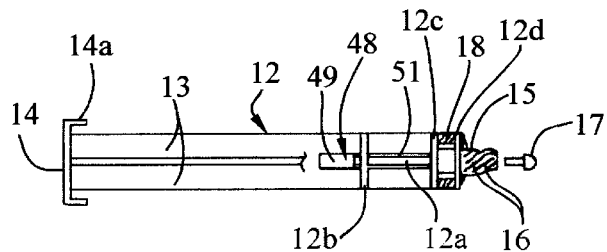
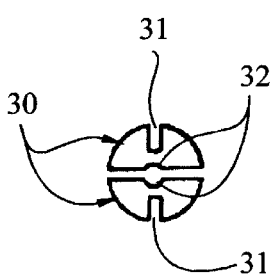
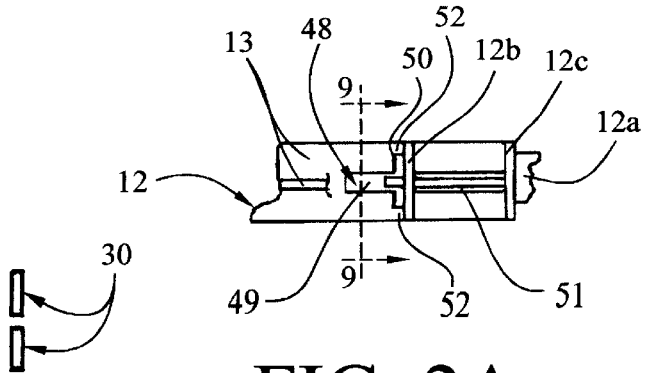
FIG. 2
FIG. 1
FIG. 3  FIG. 3A
FIG. 2A

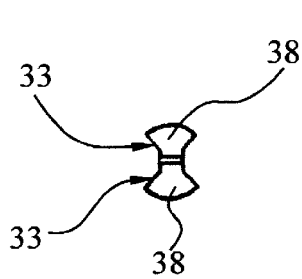
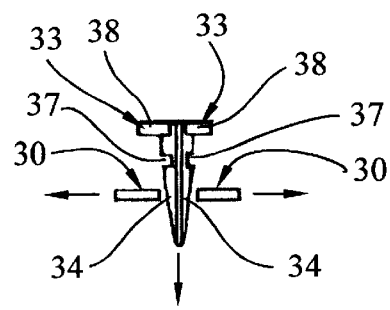
FIG. 4  FIG. 4A
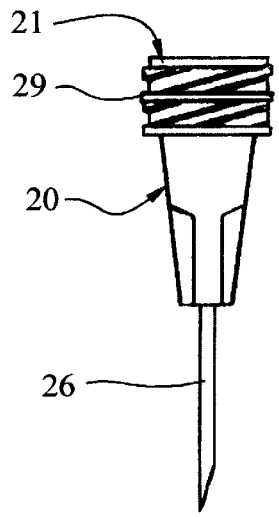
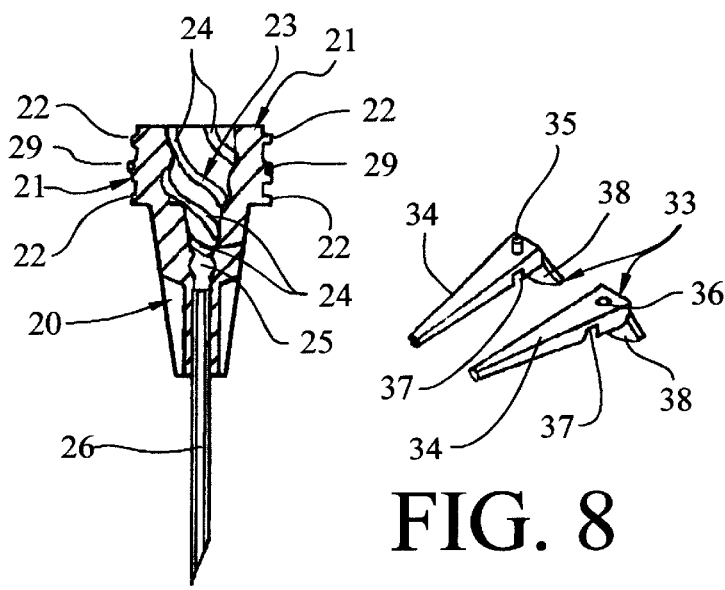
FIG. 5  FIG. 6  FIG. 8
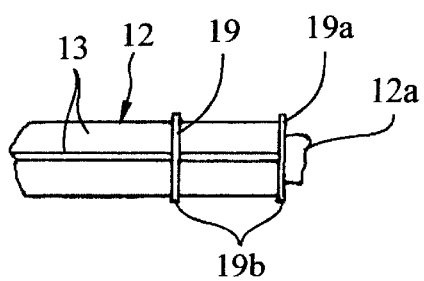
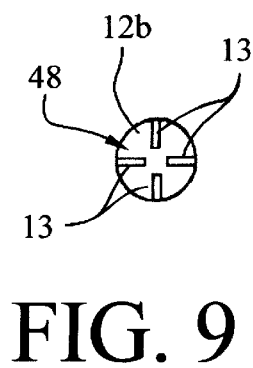
FIG. 7  FIG. 9

RETRACTABLE SYRINGE

BACKGROUND OF THE INVENTION

1. Field of the Invention

This invention relates to syringes having a retractable needle or cannula and more particularly, to a retractable syringe characterized by a syringe needle which can be retracted into the syringe and locked therein after use to prevent accidental needle sticks or re-use of the syringe. In a preferred embodiment the retractable syringe includes a syringe barrel terminated by a tapered barrel neck which communicates with the syringe barrel interior. As the barrel neck receives the needle hub of the syringe needle, the needle hub is rotated to cause engagement of barrel threads, provided on the inside surface of the barrel neck, with exterior hub threads, provided on the exterior surface of the needle hub, and secure the needle hub in the barrel neck, in confluent relationship with the syringe barrel. A syringe plunger, slidably disposed in the syringe barrel, is terminated by a plunger nipple which is fitted with exterior plunger threads for engaging interior hub threads of the needle hub. After the syringe plunger is operated in conventional fashion to expel the liquid contents of the syringe barrel through the syringe hub and needle, the plunger is rotated in the barrel to threadibly seat the plunger nipple in the needle hub. Because the barrel threads and companion exterior hub threads of the needle hub are oppositely-threaded with respect to the plunger threads and companion interior hub threads, continued rotation of the plunger in the syringe barrel threads the attached needle hub and needle rearwardly from the barrel neck into the syringe barrel interior, by operation of the interior barrel threads and companion exterior hub threads. In a preferred embodiment a plunger lock tip terminates the plunger nipple of the plunger, and seats in a tip receptacle shaped inside the needle hub to further secure the plunger nipple to the needle hub. In a first embodiment of the retractable syringe, a pair of flexible plunger lock tabs is inserted in the plunger shaft, and a locking ridge is shaped circumferentially inside the syringe barrel. After threaded retraction of the contaminated or used needle into the syringe barrel, a pair of plunger lock pins, located in a lock slot provided in the plunger between the plunger lock tabs, are positioned such that the plunger lock tabs are forced outwardly from the plunger and engage the locking ridge to hinder removal of the syringe plunger from the barrel. In a second embodiment a pair of lock plates is provided on the syringe plunger, for engaging the locking ridge and hindering withdrawal of the plunger from the barrel.

Medical treatments frequently include intravenous administration of medications using syringes and needles. Often the syringe needle remains exposed from the time of use until safe disposal of the syringe in a suitable "sharps" container, thus increasing the likelihood of accidental needle sticks during handling of the syringe. With the advent of AIDS and other blood-borne diseases such as hepatitis, the potential risk of accidental needle sticks is attended by dangerous and possibly lethal consequences to health care providers. Accordingly, the retractable syringe of this invention facilitates withdrawal of a used or contaminated syringe needle or cannula into the syringe barrel after use of the syringe in order to reduce exposure of the unprotected needle and minimize the possibility of an accidental needle stick. The retractable syringe further includes a syringe plunger locking mechanism which hinders withdrawal of the syringe plunger and retracted needle from the barrel after use of the syringe, to prevent or discourage re-use of the syringe and reduce the spread of disease resulting from "shared needles".

2. Description of the Prior Art

Syringes having retractable needles are well-known in the art. Typical of these syringes is the "Syringe with Retractable Cannula", detailed in U.S. Pat. No. 4,026,287, dated May 31, 1977, to Irene Haller. The syringe is characterized by a plunger which is slidably disposed in a syringe barrel, and the front end of the plunger can be caused to threadably engage the forward end wall of the syringe barrel by rotating the plunger in the barrel after the fluid contents of the syringe are dispensed. Subsequent retraction of the plunger into the barrel causes the perforated forward end wall of the barrel to break away from the barrel with the plunger, and the cannula, attached to the forward end wall, is retracted into the barrel. U.S. Pat. No. 4,995,874, dated Feb. 26, 1991, to H. Allen Strickland, describes a "Disposable Syringe Device" fitted with a retractable needle. The syringe includes a syringe barrel and a plunger in which a threaded extension or threadlock, provided on the forward end of the plunger, is capable of engaging a threadbare element, provided in the forward neck portion of the barrel, by rotating the plunger in the barrel after the fluid contents of the syringe are dispensed from the barrel. Because the threadbore element is secured to the needle, the needle may be withdrawn into the barrel by pulling the plunger rearwardly in the barreL A "Syringe" is disclosed in U.S. Pat. No. 5,141,495, dated Aug. 25, 1992, to Gudmar Olovson. The syringe is characterized by a syringe barrel, within which is slidably disposed a plunger terminated by a plunger piston. The plunger is provided with two sets of right-handed threads which rotate the plunger in the clockwise direction as the plunger is extended from the barrel and in the counterclockwise direction as the plunger is extended into the barrel. The plunger piston is attached to the plunger by means of left-handed threads, such that extension of the plunger from the barrel tightens the plunger piston on the plunger, whereas extension of the plunger into the barrel unthreads the plunger piston from the plunger. A set of lock tabs extends from the barrel walls into the barrel, at the needle end of the barrel for engaging the unthreaded plunger piston. As the plunger is extended into the barrel to expel the liquid syringe contents through the needle, the plunger piston becomes unthreaded from the plunger and is permanently seated in the needle end of the piston by means of the lock tabs, preventing re-use of the syringe. U.S. Pat. No. 5,417,661, dated May 23, 1995, to Jeffrey L. Stringer, et aL, describes a "Safety Syringe", characterized by a disposable safety hypodermic syringe wherein the used syringe needle is retracted into the syringe barrel by rotating the syringe plunger, and the needle is captured completely within the barrel when the plunger is retracted and locked with respect to the barrel. U.S. Pat. No. 5,533,970, dated Jul. 9, 1996, to Howard S. Berger, et al., details a "Retractable Needle Syringe" including a barrel having open front and rear ends. An elongated plunger, slidably disposed in the barrel includes a radially-extending plunger lock tab adjacent to its insertion end. A needle carrier is slidably disposed in the barrel interior at the front end thereof, and a needle cannula extends forwardly from the needle carrier, in fluid communication with the barrel interior and through the open front end of the barrel. The proximal end of the carrier includes an open-ended groove which is sized and shaped to receive the plunger lock tab. Rotation of the plunger inside the barrel causes the lock tab to enter the groove, thereby connecting the plunger with the carrier. After use of the syringe, the plunger can be extended from the syringe barrel to slide the carrier away from the front end of the barrel and retract the needle into the barrel. An "Ampule Safety Syringe" is detailed in U.S. Pat. No. 5,593,391, dated Jan. 14, 1997, to Sydney D. Stanners. The syringe is characterized by a syringe ampule or barrel having a finger grip provided on the rear end of the barrel and an elongated plunger, terminated by a plunger piston, slidably disposed in the barrel and extending through an opening provided in the finger grip. A barrel cap is affixed to the front end of the barrel, and a hollow needle extends through a needle hub which is threaded in the barrel cap. After the liquid contents of the barrel are expelled through the needle by operation of the plunger, the plunger piston engages the needle, and extension of the plunger from the barrel causes the plunger piston to draw or retract the needle into the barrel.

An object of this invention is to provide a syringe having a syringe needle which is capable of being retracted into the syringe after use.

Another object of this invention is to provide a syringe having a cannulated syringe needle which can be retracted and locked in the syringe after use in order to prevent accidental needle sticks and re-use of the syringe.

Still another object of this invention is to provide a syringe characterized by a syringe barrel, a cannulated syringe needle terminating the syringe barrel and a syringe plunger slidably disposed in the syringe barrel for expelling the liquid contents of the barrel through the needle, wherein the needle can be retracted into the barrel after use by rotating the plunger in the barrel thereby causing the plunger to first threadibly engage and seat the syringe needle and then thread the needle into the barrel as rotation of the plunger is continued.

Yet another object of this invention is to provide a syringe characterized by a syringe barrel; a cannulated syringe needle terminating the syringe barrel; and a syringe plunger slidably disposed in the syringe barrel for expelling the liquid contents of the syringe from the syringe barrel through the needle, which needle can be retracted into the barrel after use of the syringe by initially rotating the plunger in the barrel and causing the plunger to threadibly engage and seat the syringe needle, and then incrementally threadibly drawing or retracting the needle into the barrel by continued rotation of the plunger; and a pair of flexible plunger lock tabs provided on the plunger is expanded outwardly from the plunger and caused to engage a locking ridge shaped circumferentially in the plunger barrel, by a pair of plunger lock pins located in a lock slot provided in the plunger between the plunger lock tabs, thereby substantially locking the retracted needle inside the syringe barrel and preventing or hindering removal of the plunger and attached needle from the barrel.

A still further object of this invention is to provide a syringe characterized by a syringe barrel; a cannulated syringe needle terminating the syringe barrel; and a syringe plunger sidably disposed in the syringe barrel for expelling the liquid contents of the syringe from the syringe barrel through the needle, which needle can be retracted into the barrel after use of the syringe by initially rotating the plunger in the syringe barrel and causing the plunger to threadibly engage and seat the syringe needle, and then incrementally threading the needle into the barrel by continued rotation of the plunger; and at least one plunger lock plate provided on the plunger for engaging a locking ridge shaped circumferentially inside the syringe barrel, thereby substantially locking the retracted needle inside the barrel and preventing or hindering removal of the plunger and attached needle from the barreL

SUMMARY OF THE INVENTION

These and other objects of the invention are provided in a retractable syringe characterized by a syringe needle which can be retracted and locked in the syringe barrel after use, to prevent accidental needle sticks or re-use of the syringe. In a preferred embodiment the retractable syringe includes a syringe barrel terminated by a barrel neck which communicates with the syringe barrel interior. As the barrel neck receives the needle hub of the cannulated syringe needle, the needle hub is rotated to cause engagement of barrel threads, provided on the inside surface of the barrel neck, with exterior hub threads, provided on the exterior surface of the needle hub, and secure the needle hub and attached needle in the barrel neck, in confluent relationship with the syringe barrel. A syringe plunger, sidably disposed in the syringe barrel, is terminated by a plunger nipple which is fitted with exterior plunger threads for engaging interior hub threads of the needle hub. After the syringe plunger is operated in conventional fashion to expel the liquid contents of the syringe barrel through the syringe hub and needle, the plunger is rotated in the barrel to threadibly seat the plunger nipple in the needle hub. Because the barrel threads and companion exterior hub threads of the needle hub are oppositely-threaded with respect to the plunger threads and companion interior hub threads, continued rotation of the plunger in the syringe barrel threads the attached needle hub and needle rearwardly from the barrel neck into the syringe barrel interior, by operation of the interior barrel threads and companion exterior hub threads. In a preferred embodiment a plunger lock tip terminates the plunger nipple of the plunger, and seats in a tip receptacle shaped inside the needle hub to further secure the plunger nipple to the needle hub. In a first embodiment of the retractable syringe, a pair of flexible plunger lock tabs is inserted in the plunger shaft, and a locking ridge is shaped circumferentially inside the syringe barreL After threaded retraction of the used or contaminated needle into the syringe barrel, a pair of plunger lock pins, located in a lock slot provided in the plunger between the lock tabs, cause the plunger lock tabs to extend outwardly from the plunger and engage the locking ridge to prevent or hinder removal of the syringe plunger and attached needle from the barrel. In a second embodiment a pair of lock plates is provided on the syringe plunger, for engaging the locking ridge to hinder withdrawal of the plunger and needle from the barrel.

BRIEF DESCRIPTION OF THE DRAWINGS

The invention will be better understood by reference to the accompanying drawings, wherein:

FIG. 1 is an exploded, perspective view of a preferred embodiment of the retractable syringe of this invention;

FIG. 2 is an exploded, side view, partially in section, of the syringe plunger component of the retractable syringe;

FIG. 2A is a top view, partially in section, of the syringe plunger illustrated in FIG. 2;

FIG. 3 is a front view of the plunger lock tab components of a preferred embodiment of the retractable syringe, removed from the syringe plunger;

FIG. 3A is a side view of the plunger lock tabs illustrated in FIG. 3;

FIG. 4 is a flange end view of the plunger lock pin components of a preferred embodiment of the retractable syringe, with the plunger lock pins connected to each other in typical application of the retractable syringe;

FIG. 4A is a side view of the plunger lock pins illustrated in FIG. 4, more particularly illustrating insertion of the plunger lock pins between the plunger lock tabs illustrated in FIG. 3 and interconnection of the plunger lock pins to facilitate locking the syringe plunger in the syringe barrel of the retractable syringe;

FIG. 5 is a side view of the needle hub and attached cannulated needle components of the retractable syringe;

FIG. 6 is a longitudinal sectional view of the needle hub and cannulated needle illustrated in FIG. 5;

FIG. 7 is a sectional view of the syringe plunger component of another embodiment of the retractable syringe of this invention, more particularly illustrating a pair of plunger lock plates provided on the plunger for engaging a locking ridge shaped circumferentially in the plunger barrel and locking the plunger in the barrel;

FIG. 8 is a perspective view of the plunger lock pins illustrated in FIG. 4A, removed from the plunger lock tabs and disconnected from each other; and FIG. 9 is a sectional view, taken along section lines 9—9 in FIG. 2A of the syringe plunger of a preferred embodiment of the retractable syringe.

DESCRIPTION OF THE PREFERRED EMBODIMENTS

Referring initially to FIGS. 1–2A, 5, 6 and 9 of the drawing, in a preferred embodiment the retractable syringe of this invention is generally illustrated by reference numeral 1. The retractable syringe 1 includes an elongated syringe barrel 2, the front end of which is terminated by a tapered barrel neck 5, which syringe barrel 2 and barrel neck 5 are traversed by a syringe bore 3 as illustrated in FIG. 1. A pair of barrel flanges 4 is typically formed in the rear end of the syringe barrel 2, in substantially perpendicularly-extending relationship to the longitudinal axis of the syringe barrel 2. An annular locking ridge 8, shaped in the barrel wall (not illustrated) at the barrel flange 4 end of the syringe barrel 2, extends circumferentially into the syringe bore 3 for purposes which will be hereinafter further described. As further illustrated in FIG. 1, typically right-handed barrel threads 6 are provided on the interior surface of the barrel neck 5, inside the syringe bore 3, and an O-ring seal groove 7 is circumscribed in the interior surface of the barrel neck 5 for purposes which will be hereinafter further described. The barrel neck 5 of the syringe barrel 2 receives the hub base 21 of a typically plastic needle hub 20, traversed by a hub bore 23 and having a cannulated syringe needle 26 extending therefrom in confluent relationship to the hub bore 23, as illustrated in FIG. 6. Typically left-handed, interior hub threads 24, provided on the inside surface of the hub base 21, extend into the hub bore 23 for purposes which will be hereinafter further described. Typically right-handed, exterior hub threads 22 are provided on the exterior surface of the hub base 21 of the needle hub 20, for engaging the companion, right-handed barrel threads 6 in the barrel neck 5 as the needle hub 20 is rotated in the clockwise direction in the barrel neck 5, to secure the hub base 21 of the needle hub 20 in the barrel neck 5 of the syringe barrel 2 as hereinafter further described. A rubber or plastic o-ring 29, fitted in an o-ring mount groove (not illustrated) which circumscribes the hub base 21 of the needle hub 20, seats in the o-ring seal groove 7 (FIG. 1, provided in the interior surface of the barrel neck 5) and seals the hub base 21 in the barrel neck 5. Accordingly, the syringe needle 26 is disposed in confluent relationship to the syringe bore 3 of the syringe barrel 2, through the barrel neck 5 for selective expulsion of liquid from the syringe barrel 2 through the syringe needle 26, in typical application of the retractable syringe 1 as hereinafter further described. A plastic, conventional needle sheath 28 is typically inserted on the needle hub 20, over the syringe needle 26 for protective purposes.

As further illustrated in FIG. 1, an elongated, substantially cruciform-shaped, typically plastic syringe plunger 12 is slidably disposed in the syringe bore 3 of the syringe barrel 2, and is typically characterized by a pair of intersecting plunger flanges 13 which traverse the length of the syringe plunger 12. A thumb flange 14 typically terminates the plunger flanges 13 at the rear end of the syringe plunger 12, for receiving thumb pressure as the syringe plunger 12 is extended into the syringe bore 3 during operation of the retractable syringe 1, as hereinafter further described. A pair of oppositely-disposed grip flanges 14a typically project rearwardly from opposite sides of the thumb flange 14, to facilitate grasping and rotating the syringe plunger 12 in the syringe bore 3 for purposes which will be hereinafter further described. The plunger flanges 13 extend forwardly from the thumb flange 14 through a circular, rear brace flange 12b and, at the front end of the syringe plunger 12, terminate on a similar, front brace flange 12c. As illustrated in FIG. 2, a cylindrical plunger neck 12a projects concentrically from the front brace flange 12c, and terminates in a circular, concentric front end plate 12d. A typically rubber plunger piston 18 encircles the front brace flange 12c, front end plate 12d and intervening plunger neck 12a of the syringe plunger 12. The circular periphery of the plunger piston 18 achieves a fluid-tight seal with the congruent interior surface of the syringe barrel 2. A tapered plunger nipple 15, provided with typically left-handed plunger threads 16 formed in the surface thereof, extends forwardly from the front end plate 12d of the syringe plunger 12, through a nipple opening (not illustrated) provided in the leading surface of the plunger piston 18. A break-away plunger lock tip 17 typically extends from the front end of the plunger nipple 15 and is seated in a plunger tip receptacle 25 (FIG. 6), shaped in the hub bore 23 of the needle hub 20, when the hub base 21 of the needle hub 20 is threaded in the barrel neck 5, the purpose of which plunger threads 16 and plunger lock tip 17 will be hereinafter further described.

Referring next to FIGS. 1–6, 8 and 9 of the drawing, a lock slot 48 is provided in the syringe plunger 12, at the junction of the plunger flanges 13 as particularly illustrated in FIG. 9. The lock slot 48 includes a longitudinal lock pin portion 49 and a transverse lock tab portion 50 which extends a short distance into one of the plunger flanges 13 as illustrated in FIG. 2A, defining a lock tab retainer 52 at the outer edges of the plunger flange 13. The lock slot 48 extends through substantially the center of the rear brace flange 12b of the syringe plunger 12, and includes an insertion segment portion 51 which extends between the rear brace flange 12b and front brace flange 12c. As illustrated in FIG. 3, a pair of flexible, plastic, generally semicircular plunger lock tabs 30 is each provided with a rectangular tab notch 31 at substantially the midpoint of the curved edge thereof, and a lock pin notch 32 at substantially the midpoint of the straight edge thereof The plunger lock tabs 30 are inserted in the respective lock tab portions 50 of the lock slot 48, and the tab notch 31 of each plunger lock tab 30 receives the corresponding lock tab retainer 52 (FIG. 2A) of the plunger flange 13 to secure the plunger lock tab 30 in the lock tab portion 50 of the lock slot 48.

As illustrated in FIG. 8, a pair of typically plastic plunger lock pins 33 each includes an elongated, tapered insertion segment 34, having a pin notch 37 shaped in the front surface thereof and terminated on the wide end thereof by a pin flange 38. A connector tab 35 extends from the rear surface of the insertion segment 34 of one of the plunger lock pins 33, for insertion in a companion connector opening 36, provided in the rear surface of the insertion segment 34 of the other plunger lock pin 33. As hereinafter further described, after the syringe plunger 12 is extended into the syringe bore 3 of the syringe barrel 2 to expel the liquid contents (not illustrated) of the syringe barrel 2 through the syringe needle 26, the syringe plunger 12 is extended from the syringe barrel 2 until the plunger lock tabs 30 (inserted in the respective lock tab portions 50 of the lock slot 48, FIG. 2A) are located just inside the locking ridge 8 (FIG. 1) of the syringe barrel 2 and the lock pin portion 49 of the lock slot 48 is located outside the syringe bore 3. Each of the plunger lock pins 33 is extended through the lock pin portion 49 of the lock slot 48, and inserted through the lock pin notches 32 (FIG. 3) between the plunger lock tabs 30 as illustrated in FIG. 4A, and through the insertion segment portion 51 of the lock slot 48 by exerting finger pressure on the pin flanges 38. This action forces the plunger lock tabs 30 outwardly from the syringe plunger 12 as illustrated in FIG. 4A, and causes the plunger lock tabs 30 to engage or catch on the front surface of the locking ridge 8 of the syringe barrel 2, hindering removal of the syringe plunger 12 from the syringe barrel 2.

Referring again to FIGS. 1–6, 8 and 9 of the drawing, in typical application of the retractable syringe 1 the hub base 21 of the needle hub 20 is initially threaded into the barrel neck 5 of the syringe barrel 2, by rotating the hub base 21 in the clockwise direction in the barrel neck 5 and causing the right-handed exterior hub threads 22 to threadibly engage the companion, right-handed barrel threads 6 (provided on the interior surface of the barrel neck 5). The needle sheath 28 is then removed from the needle hub 20 in order to expose the syringe needle 26, which is typically inserted in a fluid medicine vial (not illustrated) containing medical fluid (not illustrated). The syringe plunger 12, slidably disposed in the syringe bore 3 of the syringe barrel 2, is extended from the syringe bore 3 to create vacuum pressure inside the syringe bore 3 and draw the medical fluid from the vial, through the syringe needle 26 and needle hub 20 and into the syringe bore 3, in conventional fashion. The syringe needle 26 of the fluid-filled retractable syringe 1 is removed from the vial and inserted into the needle port (not illustrated) of an intravenous fluid delivery system or IV, or into the patient's vein (not illustrated). While the barrel flanges 4 are grasped using the index and middle fingers, the syringe plunger 12 is advanced forwardly in the syringe bore 3 by exerting thumb pressure on the thumb flange 14, to expel the fluid contents of the syringe bore 3, through the hub bore 23 (FIG. 6) of the needle hub 20 and confluent syringe needle 26, and then into the IV fluid delivery system or patient, by operation of the plunger piston 18.

After the syringe needle 26 is removed from the IV fluid delivery system or patient, the needle hub 20 and attached syringe needle 26 are drawn or retracted into the syringe bore 3, as follows. The plunger lock tip 17 (FIG. 1) and plunger nipple 16 are inserted into the hub bore 23 of the hub base 21, and the syringe plunger 12 is rotated in the counterclockwise direction in the syringe bore 3 while grasping the grip flanges 14a, to cause the left-handed plunger threads 16 (provided on the surface of the plunger nipple 16) to threadibly engage the left-handed interior hub threads 24 of the hub base 21. This action seats the plunger nipple 15 in the hub base 21 and the plunger lock tip 17 in the plunger tip receptacle 25 (shaped in the hub bore 23 of the needle hub 20, FIG. 6). Continued counterclockwise rotation of the syringe plunger 12 in the syringe barrel 2 causes the attached hub base 21 of the needle hub 20 to likewise rotate in the counterclockwise direction in the barrel neck 5. Consequently, the right-handed barrel threads 6 and companion exterior hub threads 22 operate to draw the hub base 21 from the barrel neck 5, rearwardly into the syringe bore 3 of the syringe barrel 2, until the hub base 21 is located entirely within the syringe bore 3. Accordingly, the contaminated syringe needle 26 is safely contained in the syringe barrel 2, and as long as the syringe plunger 12 and attached needle hub 20 are rotated in the counterclockwise direction, the exterior hub threads 22 and barrel threads 6 will prevent forward threading of the needle hub 20 and syringe needle 26 through the barrel neck 5. It will be appreciated by those skilled in the art that clockwise rotation of the syringe plunger 12 and attached needle hub 20 in the syringe bore 3 will cause the plunger threads 16 of the plunger nipple 15 to become disengaged from the interior hub threads 24 of the hub base 21, and thus prevent forward threading of the needle hub 20 and syringe needle 26 through the barrel neck 5, and re-use of the retractable syringe 1.

As illustrated in FIGS. 3–4A of the drawing, in a preferred embodiment of the retractable syringe 1 the syringe plunger 12 is locked in the syringe bore 3, to prevent or hinder removal of the syringe plunger 12 and attached needle hub 20 and syringe needle 26 from the syringe barrel 2, and re-use of the retractable syringe 1. Accordingly, the insertion segments 34 (FIG. 8) of the respective plunger lock pins 33 are initially individually inserted into the lock pin portion 49 of the lock slot 48 (FIGS. 2A and 9) of the syringe plunger 12. The insertion segments 34 are then extended through the lock pin notches 32 (FIG. 3) between the respective plunger lock tabs 30, and through the open center of the rear brace flange 12b and into the insertion segment portion 51 of the lock slot 48, until the pin notches 37 (FIG. 8) of the respective plunger lock pins 33 receive the respective plunger lock tabs 30 at the lock pin notches 32. Consequently, as illustrated in FIG. 4A the tapered insertion segments 34 of the respective plunger lock pins 33 force the flexible plunger lock tabs 30 outwardly from the syringe plunger 12, and the plunger lock tabs 30 are thus positioned for engaging the locking ridge 8 (FIG. 1, formed circumferentially in the syringe barrel 3), inside the syringe bore 3. The connector tab 35 (FIG. 8) of one of the plunger lock pins 33 is then snap-fitted into the connector opening 36 of the opposite plunger lock pin 33, through the lock slot 48 to secure the plunger lock pins 33 together as illustrated in FIG. 1. The syringe plunger 12 and attached needle hub 20 and syringe needle 26 are thus substantially locked inside the syringe bore 3, since detachment of the plunger lock pins 33 from each other and from between the plunger lock tabs 30 is difficult and any attempt to remove the syringe plunger 12 from the syringe barrel 2 will cause the plunger lock tabs 30 to engage the locking ridge 8.

In the event of successful removal of the syringe plunger 12 and attached needle hub 20 and syringe needle 26 from the syringe barrel 2, re-use of the retractable syringe 1 would require removal of the needle hub 20 from the plunger nipple 15 of the syringe plunger 12, since forward threading of the needle hub 20 through the barrel neck 5 while attached to the syringe plunger 12 is prevented, as heretofore described. Accordingly, any attempt to unthread the needle hub 20 and syringe needle 26 from the removed plunger nipple 15 would cause the plunger lock tip 17 to break away from the plunger nipple 15 and remain lodged in the plunger tip receptacle 25 (FIG. 6), and would substantially impede the flow of fluid through the hub bore 23 of the needle hub 20 and through the syringe needle 26, should the hub base 21 be rethreaded in the barrel neck 5 in an attempt to re-use the retractable syringe 1.

Referring next to FIG. 7 of the drawing, in another embodiment of the retractable syringe 1 a circular rear plunger lock plate 19 and front plunger lock plate 19a are formed concentrically on the plunger flanges 13 of the syringe plunger 12, in spaced-apart relationship with respect to each other. The circular edges 19b of the rear plunger lock flange 19 and front plunger lock plate 19a, respectively, extend beyond the edges of the plunger flanges 13, and the rear plunger lock plate 19, located inside the syringe bore 3 of the syringe barrel 2, forwardly of the locking ridge 8, engages the front surface of the locking ridge 8 to halt extension and removal of the syringe plunger 12 from the syringe barrel 2. The rear plunger lock plate 19 thus hinders removal of the syringe plunger 12 and attached needle hub 20 and syringe needle 26 from the syringe barrel 2, after the used or contaminated syringe needle 26 is retracted into the syringe barrel 2 as heretofore described. Should the rear plunger lock plate 19 be successfully pulled rearwardly from the syringe barrel 2 beyond the locking ridge 8, the front plunger lock plate 19a then engages the front surface of the locking ridge 8 and hinders complete removal of the syringe plunger 12, needle hub 20 and syringe needle 26 from the syringe barrel 2.

It will be appreciated by those skilled in the art that the retractable syringe of this invention is characterized by a syringe needle which can be retracted into the syringe barrel and substantially locked therein in order to prevent accidental needle sticks and prevent or hinder re-use of the syringe. Referring again to FIG. 1 of the drawing, while the preferred embodiment of the retractable syringe 1 has been described above as having left-handed plunger threads 16 for engaging left-handed interior hub threads 24, and right-handed exterior hub threads 22 for engaging right-handed barrel threads 6, it is understood that the retractable syringe 1 can be constructed using right-handed plunger threads 16 and hub threads 24 as long as the exterior hub threads 22 and barrel threads 6 are left-handed. Opposite-threading of the plunger threads 16 and interior hub threads 24 with respect to the exterior hub threads 22 and barrel threads 6, facilitates seating of the plunger nipple 15 in the hub base 21 of the needle hub 20 and reverse threading of the needle hub 20 and syringe needle 26 through the barrel neck 5 into the syringe barrel 2 as the syringe plunger 12 is rotated in one direction, while causing unthreading of the plunger nipple 15 from the retracted needle hub 20 as the syringe plunger 12 is rotated in the opposite direction. It will be further appreciated by those skilled in the art that the break-away feature of the plunger lock tip 17 described above with respect to FIGS. 1 and 6, hinders re-use of both embodiments of the retractable syringe 1 illustrated in FIGS. 1–9, should the syringe plunger 12, needle hub 20 and syringe needle 26 be successfully removed from the syringe barrel 2 and the needle hub 20 re-threaded in the barrel neck 5 in an attempt to re-use the retractable syringe 1. In that case, removal of the needle hub 20 from the plunger nipple 15 causes the plunger lock tip 17 to remain lodged in the plunger tip receptacle 25 (FIG. 6) of the needle hub 20, and the tight fit of the plunger lock tip 17 in the plunger tip receptacle 25 substantially impedes flow of fluid from the syringe barrel 2, through the needle hub 20 and syringe needle 26.

While the preferred embodiments of the invention have been described above, it will be recognized and understood that various modifications can be made and the appended claims are intended to cover all such modifications which may fall within the spirit and scope of the invention.

Having described my invention with the particulaity set forth above, what is claimed is:

1. A retractable syringe comprising a needle hub having interior hub threads and exterior hub threads; a syringe barrel for receiving said needle hub and barrel threads provided in said syringe barrel for engaging said exterior hub threads of said needle hub; a syringe plunger slidably disposed in said syringe barrel and plunger threads provided on said syringe plunger for engaging said interior hub threads of said needle hub, wherein said barrel threads and said exterior hub threads are oppositely-threaded with respect to said plunger threads and said interior hub threads, whereby said syringe plunger is rotated inside said syringe barrel for engaging said plunger threads with said interior hub threads, and continued rotation of said syringe plunger and said needle hub draws said needle hub inside said syringe barrel.

2. The retractable syringe of claim 1 comprising an o-ring circumscribing said needle hub for sealing said needle hub in said syringe barrel.

3. The retractable syringe of claim 1 comprising barrel flanges provided on said syringe barrel.

4. The retractable syringe of claim 1 comprising an o-ring circumscribing said needle hub for sealing said needle hub in said syringe barrel and barrel flanges provided on said syringe barrel.

5. The retractable syringe of claim 1 comprising a plunger tip terminating said syringe plunger and a plunger tip receptacle shaped in said needle hub for receiving said plunger tip.

6. The retractable syringe of claim 5 comprising an o-ring circumscribing said needle hub for sealing said needle hub in said syringe barrel.

7. The retractable syringe of claim 5 comprising barrel flanges provided on said syringe barrel.

8. The retractable syringe of claim 5 comprising an o-ring circumscribing said needle hub for sealing said needle hub in said syringe barrel and barrel flanges provided on said syringe barrel.

9. The retractable syringe of claim 1 comprising a locking ridge provided inside said syringe barrel and at least one lock plate provided on said syringe plunger for engaging said locking ridge and substantially locking said syringe plunger inside said syringe barrel.

10. The retractable syringe of claim 9 comprising an o-ring circumscribing said needle hub for sealing said needle hub in said syringe barrel.

11. The retractable syringe of claim 9 comprising a plunger tip terminating said syringe plunger and a plunger tip receptacle shaped in said needle hub for receiving said plunger tip.

12. The retractable syringe of claim 9 comprising an o-ring circumscribing said needle hub for sealing said needle hub in said syringe barrel, a plunger tip terminating said syringe plunger and a plunger tip receptacle shaped in said needle hub for receiving said plunger tip.

13. The retractable syringe of claim 9 comprising barrel flanges provided on said syringe barrel.

14. The retractable syringe of claim 13 comprising an o-ring circumscribing said needle hub for sealing said needle hub in said syringe barrel.

15. The retractable syringe of claim 13 comprising a plunger tip terminating said syringe plunger and a plunger tip receptacle shaped in said needle hub for receiving said plunger tip.

16. The retractable syringe of claim 13 comprising an o-ring circumscribing said needle hub for sealing said needle hub in said syringe barrel, a plunger tip terminating said syringe plunger and a plunger tip receptacle shaped in said needle hub for receiving said plunger tip.

17. A retractable syringe comprising a needle hub having interior hub threads and exterior hub threads; a syringe barrel, a barrel neck terminating said syringe barrel for receiving said needle hub and barrel threads provided in said barrel neck for engaging said exterior hub threads of said needle hub; a syringe plunger slidably disposed in said syringe barrel and plunger threads provided on the end of said syringe plunger for engaging said interior hub threads of said needle hub, wherein said barrel threads and said exterior hub threads are oppositely-threaded with respect to said plunger threads and said interior hub threads, whereby said syringe plunger is rotated inside said syringe barrel for engaging said plunger threads with said interior hub threads and seating said syringe plunger in said needle hub, and continued rotation of said syringe plunger and said needle hub draws said needle hub inside said syringe barrel; a locking ridge shaped in said syringe barrel, a lock plate provided on said syringe plunger, a pair of plunger lock tabs provided on said syringe plunger adjacent to said lock plate and a pair of plunger lock pins for insertion between said plunger lock tabs, respectively, and said plunger syringe, whereby said plunger lock tabs engage said locking ridge and lock said syringe plunger inside said syringe barrel.

18. The retractable syringe of claim 17 comprising a plunger tip terminating said syringe plunger and a plunger tip receptacle shaped in said needle hub for receiving said plunger tip.

19. The retractable syringe of claim 18 comprising an o-ring circumscribing said needle hub for sealing said needle hub in said syringe barrel.

20. A retractable syringe comprising a needle hub having interior hub threads and exterior hub threads; a syringe barrel, a barrel neck terminating said syringe barrel for receiving said needle hub and barrel threads provided in said barrel neck for engaging said exterior hub threads of said needle hub; a syringe plunger slidably disposed in said syringe barrel and plunger threads provided on the end of said syringe plunger for engaging said interior hub threads of said needle hub, wherein said barrel threads and said exterior hub threads are oppositely-threaded with respect to said plunger threads and said interior hub threads, whereby said syringe plunger is rotated inside said syringe barrel for engaging said plunger threads with said interior hub threads and seating said syringe plunger in said needle hub, and continued rotation of said syringe plunger and said needle hub draws said needle hub inside said syringe barrel; and a locking ridge shaped inside said syringe barrel and a plurality of lock plates provided on said syringe plunger for engaging said locking ridge and substantially locking said syringe plunger inside said syringe barrel.

* * * * *